US012622880B2

(12) United States Patent
Meinel et al.

(10) Patent No.: US 12,622,880 B2
(45) Date of Patent: May 12, 2026

(54) THERAPEUTIC SYSTEM FOR THE TOPICAL, TRANSDERMAL AND TRANSCUTANEOUS APPLICATION OF CARBON MONOXIDE

(71) Applicant: Julius-Maximilians-Universitaet Wuerzburg, Wuerzburg (DE)

(72) Inventors: Lorenz Meinel, Wuerzburg (DE); Matthias Ruopp, Wuerzburg (DE); Wolfgang Schmehl, Gruenwald (DE); Marcus Otto Gutmann, Gerbrunn (DE)

(73) Assignee: Julius-Maximilians-Universitaet Wuerzburg, Wuerzburg (DE)

( * ) Notice: Subject to any disclaimer, the term of this patent is extended or adjusted under 35 U.S.C. 154(b) by 589 days.

(21) Appl. No.: 17/911,327

(22) PCT Filed: Mar. 12, 2021

(86) PCT No.: PCT/EP2021/056296
§ 371 (c)(1),
(2) Date: Sep. 13, 2022

(87) PCT Pub. No.: WO2021/180908
PCT Pub. Date: Sep. 16, 2021

(65) Prior Publication Data

US 2023/0112937 A1 Apr. 13, 2023

(30) Foreign Application Priority Data

Mar. 13, 2020 (EP) .................................... 20162912

(51) Int. Cl.
*A61K 9/70* (2006.01)
*A61K 9/00* (2006.01)
*A61K 33/26* (2006.01)

(52) U.S. Cl.
CPC .......... *A61K 9/7092* (2013.01); *A61K 9/0019* (2013.01); *A61K 33/26* (2013.01)

(58) Field of Classification Search
CPC ..... A61K 9/7092; A61K 9/0019; A61K 33/26
See application file for complete search history.

(56) References Cited

U.S. PATENT DOCUMENTS

| | | | | |
|---|---|---|---|---|
| 5,882,674 A * | 3/1999 | Herrmann | ................. | A61P 9/10 424/448 |
| 2018/0271086 A1 | 9/2018 | Meinel et al. | | |

FOREIGN PATENT DOCUMENTS

| | | | | |
|---|---|---|---|---|
| EP | 3524290 A1 * | 8/2019 | ............. | A61K 33/00 |
| WO | WO 2002/092075 A2 | 11/2002 | | |
| WO | WO 2011/082375 A2 | 7/2011 | | |
| WO | WO-2015188941 A1 * | 12/2015 | .............. | A61P 29/02 |

OTHER PUBLICATIONS

Jakob Wollborn et al., *Journal of Controlled Release*, vol. 279, pp. 336-344 (Jun. 1, 2019).

* cited by examiner

*Primary Examiner* — Robert A Wax
*Assistant Examiner* — John W Lippert, III
(74) *Attorney, Agent, or Firm* — Smith Patent, LLC; Chalin A. Smith

(57) ABSTRACT

The present invention discloses a therapeutic system for the topic, transdermal and transcutaneous application of carbon monoxide (CO), comprising: (i) an adhesive layer, (ii) a gas-permeable and liquid- and solid-impermeable membrane, (iii) a reaction chamber comprising a CO releasing molecule A, and (iv) a gas-impermeable backing layer, wherein the transdermal therapeutic system is configured that the CO releasing molecule A can be brought into contact with a CO release triggering compound B in the reaction chamber (iii). The therapeutic system can be used for the treatment of wounds, inflammatory diseases of the skin, and inflammatory diseases of subcutaneous skin tissue, joints and tendons.

20 Claims, 7 Drawing Sheets

THERAPEUTIC SYSTEM FOR THE TOPICAL, TRANSDERMAL AND TRANSCUTANEOUS APPLICATION OF CARBON MONOXIDE

PRIORITY

This application corresponds to the U.S. National Phase of International Application No. PCT/EP2021/056296, filed Mar. 12, 2021, which, in turn, claims priority to European Patent Application No. 20162912.8 filed Mar. 13, 2020, the contents of which are incorporated by reference herein in their entirety.

TECHNICAL FIELD

The present invention is directed to a therapeutic system for the topic, transdermal and transcutaneous application of carbon monoxide and use thereof in the treatment of wounds and inflammatory diseases of the skin, subcutaneous tissue, tendons and joints, as well as of the eye. The present invention also concerns a kit comprising the transdermal therapeutic system and an injection device such as a syringe.

BACKGROUND

Chronic and non-healing wounds represent a substantial economic burden for the health system causing high annual costs. They also affect the quality of life of patients and often precede serious events such as limp amputations or even premature death.

The most serious challenge to be avoided in the treatment of wounds is the infection of the wound. This is often done via topically applied antimicrobials such as silver particles and antibiotics. Silver nanoparticles, however, show geno-toxic and cytotoxic effects on host cells and, like antibiotics, are aimed merely at the prevention of infections without supporting angiogenesis and proliferation and migration of fibroblasts, which are important for wound healing. In addition, the frequent application of antibiotics can lead to renal disease and the onset of contact dermatitis with further stress on the patient.

In order to avoid such complications, the use of nitric oxide (NO) as gaso-transmitter for improved wound healing has been studied for years. NO, with its antimicrobial properties, such as the classic substances mentioned above, supports the prevention of wound infections, which can accelerate the healing process of the wound.

In addition to prevention of infections, processes such as the aforementioned angiogenesis, proliferation of fibro-blasts, and transport of chemokines and nutrients into the wound, are also critical for a successful closure of the wound. Carbon monoxide (CO) is an interesting candidate for improved wound healing properties over NO due to its antimicrobial and anti-inflammatory properties and its good tissue penetration properties.

These properties make CO not only interesting as active agent for the treatment of open wounds, but also for the treatment of inflammatory diseases of the skin as well as subcutaneous tissue, joints and tendons, as well as of the eye.

Systemic tests have shown, however, that CO is bound very rapidly by hemoglobin under CO-Hb formation. Therefore, high doses are necessary to achieve a therapeutic effect. This, however, enhances the risk of CO poisoning of the patient. Therefore, methods have been developed in recent years to transport CO targeted to the site of action. Steiger et al. developed oral delivery systems that release CO after activation with an activating fluid, allowing for the local release of CO gas in the stomach and intestines at the damaged sites (see for example: WO 2015/188941 A1; C. Steiger et al., "Oral drug delivery of therapeutic gases—Carbon monoxide release for gastrointestinal diseases", Journal of Controlled Release, 189 (2014), 46-53; and C. Steiger et al., "Prevention of colitis by controlled oral drug delivery of carbon monoxide", Journal of Controlled Release, 239 (2016), 128-136).

Such oral systems, however, only function inside the patient and do not provide means of treating skin wounds or underlying tissue, tendons or joints. Problematic in the treatment of open wounds with CO releasing molecules (CORMs) is that the wound and thus also the organism is in direct contact with the CORM. Such molecules frequently show toxic side effects, particularly if they contain metals such as e.g. ruthenium or molybdenum. Therefore, direct contact with a CORM via the skin, let alone via an open wound, should be avoided.

WO 95/35105 A1 discloses a transdermal therapeutic system for the systemic administration of CO using CO releasing molecules, such as iron pentacarbonyl. However, in the system according to WO 95/35105 A1, contact of the patient with the CO releasing molecule is not avoided—to the contrary, while release of the CO releasing molecule from the system is controlled by a polymer matrix, it is required that the CO releasing molecule enters the organism in order to release CO into the systemic cycle. The TTS according to WO 95/35105 A1 does not provide a means for activating CO release outside the patient's body and is not suitable to protect the patient from contact with the CO releasing molecule and toxic degradation products resulting therefrom.

It is thus the object of the present invention to provide a simple and safe system for the topic, transdermal and transcutaneous application of CO, which is particularly useful for the treatment of open wounds, as well as inflammatory diseases of the skin, subcutaneous tissue, tendons and joints associated therewith, as well as of the eye. Such a system should combine the physiological benefits of CO, the avoidance of systemic generation of CO-Hb and the risks associated therewith, and the prevention of contact, in particular open wound contact with potentially toxic CORMs and their degradation products after CO release.

WO 2016/110517 A1 discloses a gas delivery device, wherein the problem of toxicity derived from degradation products of the gas releasing compounds is addressed by using a gas permeable and liquid and solid impermeable membrane, e.g. a silicone membrane that prevents toxic degradation products from leaving the device. However, the gas delivery device disclosed in WO 2016/110517 A1 is not suitable for therapeutic purposes, and does not make a suggestion for the topic, transdermal and transcutaneous application of CO. Rather, this device is intended for gas delivery to extra-corporeal transplants, extra-corporeal cells, a brain-dead transplant or food stuff.

DE 10 2017 006 393 A1 discloses CO releasing systems comprising a metal carbonyl compound and a triggering compound, which are suitable for use in therapy. However, this document does not disclose a method to administer the CO releasing system to a patient in order to benefit from its therapeutic potential, let alone by means of a transdermal therapeutic system that is designed in order to avoid contact of the patient's body with the toxic metal carbonyl compound and its degradation products that are formed upon contact with the triggering compound.

SUMMARY OF THE INVENTION

The object underlying the present invention is solved by:

1. Therapeutic system for the topic, transdermal and transcutaneous application of carbon monoxide (CO), comprising:
   (i) an adhesive layer,
   (ii) a gas-permeable and liquid- and solid-impermeable membrane,
   (iii) a reaction chamber comprising a CO releasing molecule A,
   (iv) a gas-impermeable backing layer,
   wherein the transdermal therapeutic system is configured that the CO releasing molecule A can be brought into contact with a CO release triggering compound B in the reaction chamber (iii).
2. Therapeutic system according to item 1, wherein the membrane (ii) is a lower membrane and the system additionally comprises a liquid- and solid-impermeable upper membrane (v) between the reaction chamber (iii) and the backing layer (iv).
3. Therapeutic system according to any of the preceding items, wherein the reaction chamber (iii) is surrounded by a spacer (vi).
4. Therapeutic system according to any of the preceding items, wherein the membrane consists of expanded polytetrafluoroethylene or silicone, and preferably of silicone.
5. Therapeutic system according to any of the preceding items, wherein the reaction chamber (iii) is a one-compartment reaction chamber and the therapeutic system further comprises a luer-lock connection (vii) or a septum (vii), allowing addition of a CO release triggering compound B into the reaction chamber (iii).
6. Therapeutic system according to items 1 to 4, wherein the reaction chamber (iii) is a two-compartment reaction chamber divided by a partition wall (viii), wherein one compartment comprises the CO releasing molecule A, and the other compartment comprises the CO release triggering compound B and wherein said partition wall is removable.
7. Therapeutic system according to any of the preceding items, wherein the adhesive layer is protected by a release liner during storage of the therapeutic system.
8. Therapeutic system according to any of the preceding items, wherein the CO releasing molecule A is a metal carbonyl compound, preferably a molybdenum carbonyl compound.
9. Therapeutic system according to any of the preceding items, wherein the CO release triggering compound B is a sulfur containing compound, a nitrogen containing compound, an oxidizing compound, a metal salt selected from the group of oxidizing and non-oxidizing metal salts, or water.
10. Therapeutic system according to any of the preceding items, wherein the CO releasing molecule A is a molybdenum carbonyl compound, preferably $Mo(CO)_3(CNCH_2CO_2H)_3$, and the CO release triggering compound B is $FeCl_3$, $Ce(SO_4)_2$ or $H_2O_2$, preferably $FeCl_3$.
11. Therapeutic system according to any of the preceding items, wherein the CO releasing molecule A is used in form of a powder or tablet and/or the CO release triggering compound B is used in form of an aqueous solution or suspension.
12. Therapeutic system according to any of the preceding items for use in the treatment of wounds.
13. Therapeutic system according to any of the preceding items for use in the treatment of inflammatory diseases of the skin, preferably of dermatitis and eczema.
14. Therapeutic system according to any of the preceding items for use in the treatment of inflammatory diseases of subcutaneous skin tissue, tendons and/or joints, preferably of gout and tendonitis.
15. Therapeutic system according to any of the preceding items for use in the treatment of inflammatory diseases of the eye.
16. Kit comprising the therapeutic system according to items 1 to 5 and 7 to 15 and an injection device, preferably a syringe, wherein said injection device comprises an aqueous solution of the CO release triggering compound B.

DETAILED DESCRIPTION OF THE INVENTION

Figure 1A:
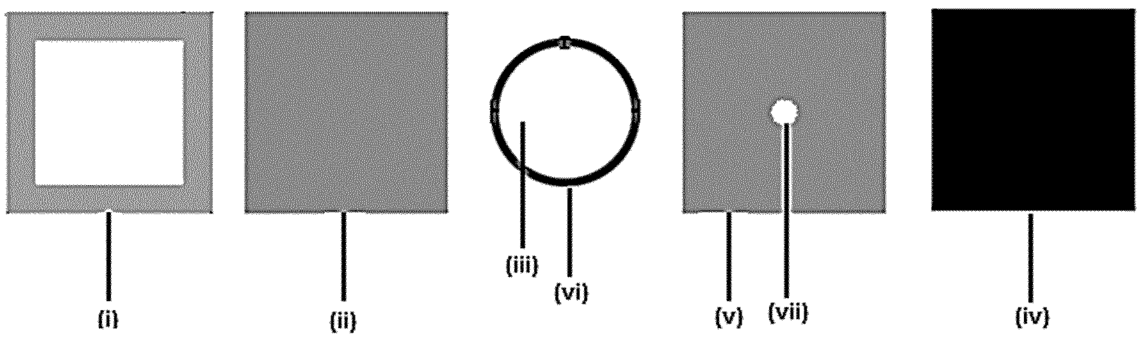
FIG. 1*a* illustrates the different layers in a preferred embodiment of the therapeutic system of the present invention, comprising: an adhesive layer (i), a gas-permeable and liquid- and solid-impermeable lower membrane (ii), the reaction chamber (iii) surrounded by a spacer (vi), a liquid- and solid-impermeable upper membrane (v) with a luer-lock connection or septum (vii) incorporated therein, and a gas-impermeable backing layer (iv).
Figure 1B:
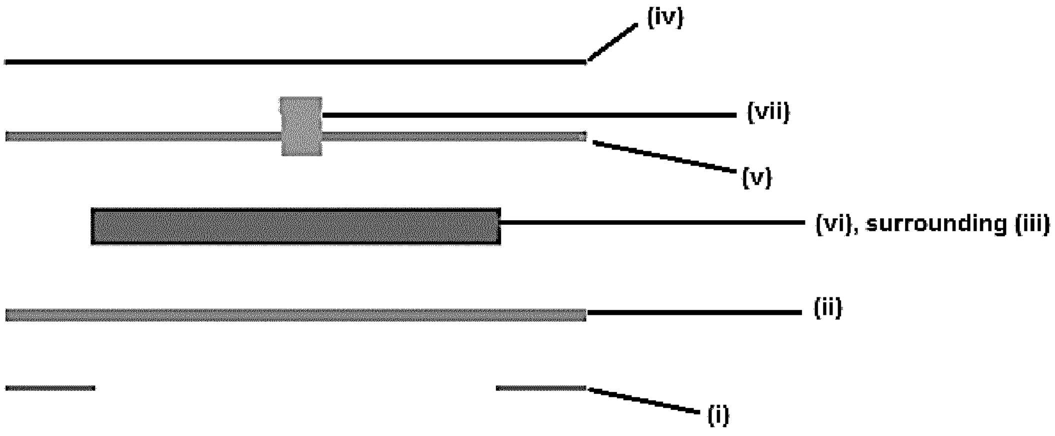
FIG. 1*b* is a schematic side view on (i)-(vii).
Figure 2:
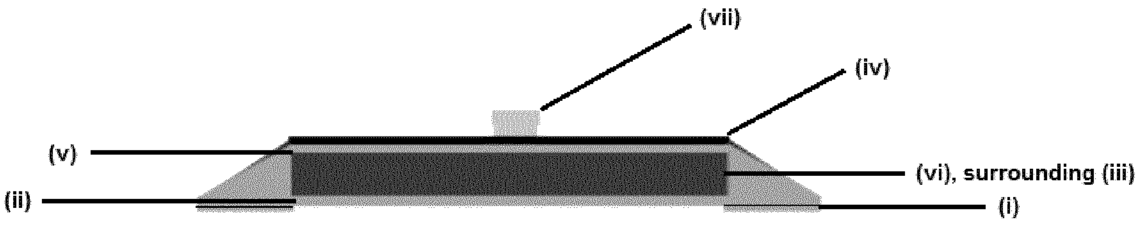
FIG. 2 is a side view on an exemplary one-compartment embodiment of the therapeutic system of the present invention comprising (i)-(vii), wherein in accordance with one embodiment of the present invention, the lower membrane (ii) and the upper membrane (v) are connected to form the same component surrounding the spacer (vi).

In the therapeutic system of the present invention, "bottom" refers to the layer which is in contact with the patient's body when the system is in use (which is the adhesive layer (i)), and "top" refers to the layer, which is furthest removed from the patient when the system is in use (which is the backing layer (iv)). The order of layers (i) to (iv) is thus from "bottom" to "top" of the system of the present invention.

The therapeutic system of the present invention can also be designated as "patch" for the topic, transdermal and transcutaneous application of carbon monoxide (CO). The "topic application of CO" as used in the present invention means the application of CO to targets sites on the skin, such as open wounds and parts of the skin that are infected by an inflammatory skin disease. The "transdermal application of CO" as used in the present invention means the application of CO into subcutaneous skin tissue. The "transcutaneous application of CO" as used in the present invention means the application of CO into subcutaneous skin tissue as well as to joints and tendons through the skin. The terms "transdermal" and "transcutaneous" application can thus be used synonymously in parts.

The topic, transdermal and transcutaneous application of carbon monoxide by means of the therapeutic system of the present invention also includes applications to the eye and the different skins of the eye, respectively. The skins of the eye include the cornea, iris, sclera, choroidea, retina, and corpus ciliare. Using the therapeutic system of the present invention, both topic and subcutaneous tissue of the eye can be administered with CO quickly and efficiently. CO is able to diffuse through intact layers of the eye and to accumulate in the disease tissue of the eye, where it develops its anti-inflammatory properties.

Inflammation of the eye often occurs idiopathically without any associations with infections or systemic diseases. In that case, a symptomatic therapeutic approach is normally used. The standard symptomatic therapy involves corticoids and non-steroidal anti-inflammatory drugs which have the disadvantage to have side effects. The advantage of using the therapeutic system of the present invention for treating inflammatory diseases of the eye compared to the standard therapies lies in the rapid bioavailability of the therapeutic agent CO and a significantly lower side effect profile.

In the system of the present invention, CO is generated from a CO releasing molecule A (CORM) by on-demand and in-situ activation using a CO release triggering compound B. Transport and storage of the therapeutic system of the present invention takes place in the non-activated state, wherein the CO releasing molecule A and the CO release triggering compound B are physically separated from each other. In order to activate the therapeutic system of the present invention, the CO releasing molecule A is brought into contact with a CO release triggering compound B in the reaction chamber (iii) of the therapeutic system of the present invention. It will be apparent from the following description how this can be achieved.

The characterization of the transdermal therapeutic system as "being configured that the CO releasing molecule A can be brought into contact with a CO release triggering compound B in the reaction chamber (iii)" thus means that CO release from the transdermal therapeutic system is activated (initiated) by bringing the CO releasing molecule A into contact with a CO release triggering compound B in the reaction chamber (iii).

The system can either be activated by a patient or by a health care professional after attaching the therapeutic system to the target site on the patient's skin or the patient's eye via the adhesive layer (i) of the therapeutic system. The adhesive layer (i) thus serves to fix the therapeutic system to the skin or the eye of the patient, and furthermore centers the CO release to the target site, such as an open wound, on the patient's body.

The adhesive layer (i) does not entirely cover the membrane (ii) of the therapeutic system of the present invention in order to ensure that CO is released from the reaction chamber (iii) through the membrane (ii) to the target site of the patient's body. Accordingly, the adhesive layer (i) may for example comprise a variety of openings. Alternatively, it can be used in form of stripes or crosses attached to the membrane (ii). Preferably, it is used in form of a belt surrounding the membrane (ii).

The adhesive layer (i) is generally made of a material which adheres to the skin or the eye of a patient and which is tolerated by the skin or the eye of the patient. Such materials include, but are not limited to, polyacrylates, polyisobutylen and silicones. In the present invention, polyacrylates are the preferred materials for the adhesive layer. The adhesive layer (i) typically has a thickness of 0.1-0.4 mm in the system of the present invention, preferably of 0.15-0.35 mm, more preferably 0.15-0.25 mm.

The adhesive layer (i) is adhered to the gas-permeable and liquid- and solid-impermeable membrane (ii) by means of an adhesive material which covers the side of the adhesive layer that is not in contact with the skin or the eye during use of the therapeutic system. The adhesive material used for this purpose is typically a silicone adhesive.

In order to protect the adhesive layer (i) of the therapeutic system during storage, the side of the adhesive layer, which is in contact with the skin or the eye of the patient during use of the system, is preferably covered with a release liner that can be removed before use of the system. The release liner is a protective layer that can be removed before attaching the system to the patient's body. Typical materials for the release liner are e.g. aluminum foil, (co)polymers selected from polyurethane, polyvinylacetate, polyethylene, polypropylene, polycarbonate, polystyrene, polyethylene terephthalate, polybutylene terephthalate, polytetrafluoroethylene (PTFE), polyester, and paper, optionally surface coated with a polymer.

CO is released from the therapeutic system to the target site of the patient's body via the gas-permeable and liquid- and solid-impermeable membrane (ii). This membrane ensures that the target site on the patient's body, in particular an open wound, is properly covered and does not come into direct contact with the CO releasing molecule A and its degradation products resulting from the reaction with the CO release triggering compound B. The CO released in the reaction of the CO releasing molecule A with the CO release triggering compound B diffuses through the gas-permeable and liquid- and solid-impermeable membrane directly into an open wound of the patient or into subcutaneous tissue under the skin or tendons and joints, or the eye. "Liquid-impermeable" means in particular that the membrane is impermeable for water and aqueous solutions or suspensions.

The membrane (ii) thus allows the CO gas to escape from the system of the present invention and to penetrate the skin barrier to unfold its effect in a wound or on the skin, subcutaneous tissue, tendons, and joints, or the eye, avoiding at the same time that the patient comes into contact with potentially toxic compounds used for the generation of CO or resulting from this reaction. The membrane (ii) necessarily forms a barrier between the skin or the eye of the patient to which the system of the present invention is adhered and the reaction chamber (iii) where CO generation takes place. Thereby, contact of the patient with toxic compounds used for the generation of CO in the reaction chamber (iii) and toxic degradation products resulting therefrom is avoided.

Accordingly, the therapeutic system of the present invention enables a safe application of CO.

Suitable materials for the gas-permeable, but liquid- and solid-impermeable membrane (ii) used in the system of the present invention, without being limited to them, include expanded polytetrafluoroethylene (ePTFE) and silicone, wherein silicone is preferred. The membrane (ii) typically has a thickness of 0.3-0.7 mm, preferably of 0.35-0.65 mm, more preferably 0.4-0.6 mm.

The reaction chamber (iii) is completely surrounded by liquid- and solid-impermeable materials (wherein liquid-impermeable in particular means impermeable for water and aqueous solutions or suspensions). The therapeutic CO generated in the reaction chamber (iii) is released through the gas-permeable and liquid- and solid-impermeable membrane (ii) from the reaction chamber (iii), and is thereby administered to the patient wearing the therapeutic system of the present invention. Reactants used in and degradation products resulting from the CO generation stay in the reaction chamber (iii).

The reaction chamber (iii) can for example be integrated into the membrane (ii) (which then comprises a space forming the reaction chamber (iii)). Liquids and solids are then retained in the reaction chamber (iii) which is surrounded by membrane (ii) and closed towards the top of the system by the gas-impermeable backing layer (iv), which is also liquid- and solid-impermeable (wherein liquid-impermeable in particular means impermeable for water and aqueous solutions or suspensions).

In a preferred embodiment of the present invention, the therapeutic system comprises a further layer of a gas-permeable and liquid- and solid-impermeable membrane between the reaction chamber (iii) and the backing layer (iv), which can also be designated as “upper” membrane (v) (and the membrane (ii) then as the “lower” membrane). The “upper” membrane typically has a thickness of 0.3-0.7 mm in the system of the present invention, preferably of 0.35-0.65 mm, more preferably 0.4-0.6 mm. In this embodiment, the reaction chamber (iii) can also be integrated into the upper membrane (v) (which then comprises a space forming the reaction chamber (iii)).

The reaction chamber (iii) can also be integrated into both the upper membrane (v) and the lower membrane (ii) (which means that both upper and lower membrane comprise a space forming the reaction chamber (iii)). This embodiment can also be executed in that the lower membrane (ii) and the upper membrane (v) form the same component, which means that the lower membrane and upper membrane are made of the same material and are connected to each other forming one component, thereby surrounding the reaction chamber (iii) and the spacer (vi), respectively.

Preferably, the reaction chamber (iii) is horizontally surrounded by a spacer (vi), which reinforces the reaction chamber in the therapeutic system. The spacer (vi) can e.g. have a cylindrical or cuboidal shape, pointing with an open end towards the membrane (ii), thereby allowing CO release from the reaction chamber (iii) through the membrane (ii) to the target site of the patient’s body. The spacer (vi) is typically made of a material that can easily be adhered with the components surrounding the spacer. Typically the spacer is made of silicone, which can be adhered to the components souring the spacer using a silicone adhesive. Silicone as the material for the spacer also has the advantage that, while it reinforces the reaction chamber, it also maintains flexibility of the therapeutic systems which allows optimal coverage of the target site on the patient’s skin or eye, such as a wound or an inflammatory site.

The spacer (vi) typically has a thickness (which means edge length in a cylinder and height in a cuboid) of 2-5 mm in the system of the present invention, preferably of 2.5-4.5 mm, more preferably of 3-4 mm. A cylindrical spacer (vi) typically has a diameter of 20-50 mm, preferably 25-45 mm, more preferably 30-40 mm. A cuboidal spacer (vi) typically has an edge length of 20-50 mm×20-50 mm, preferably 25-45 mm, more preferably 30-40 mm.

The reaction chamber (iii) comprises the CO releasing molecule A, which can be used in solid or liquid form in the system of the present invention, depending on the physical state of compound A under standard conditions (1013 hPa, 23° C.). Alternatively, it can also be used in form of an aqueous solution or suspension. Preferably, compound A is used in solid form in the system of the present invention. In that case, it can be used in a non-compressed form (e.g. as a powder), which increases the release rate. Alternatively, it can be used in a pre-compressed form (e.g. as a tablet), eventually further comprising a coating, which decreases the release rate of the CO therapeutic gas from the system of the present invention, and which ultimately allows tailoring of the release rate from the therapeutic system.

Compound B can also be used in solid or liquid form, depending on its physical state under standard conditions, or in solubilized form in the system of the present invention. Using compound B in aqueous solution or suspension is preferred because this increases the rate of the chemical reaction between compound A and compound B, in particular if compound A is used in solid form, which is also preferable. The release rate of the therapeutic gas from the system is also controlled by the characteristics of the membrane (ii), in particular its thickness.

In a first embodiment of the present invention, the reaction chamber (iii) is executed as a one-compartment reaction chamber comprising the CO releasing molecule A (“one-compartment embodiment”). In this embodiment, the CO release triggering compound B is added as an aqueous solution or suspension to the reaction chamber (iii) by means of an injection device, which is preferably a syringe. For this purpose, the therapeutic system preferably comprises a luer-lock connection (vii) or a septum (vii), which gives access to the reaction chamber of the therapeutic system of the present invention and enables the addition of the CO release triggering compound B into the reaction chamber (iii). The system of the present invention is then preferably provided with a membrane (ii) surrounding the reaction chamber (iii), and the luer-lock connection (vii) and septum (vii), respectively, are integrated into the membrane (ii) and the backing layer (iv), thereby giving an injection device such as a syringe easy access to the reaction chamber (iii). In order to avoid loss of CO through the luer-lock connection after injection of CO release triggering compound B, it is closed using a sealing. A septum is gas-impermeable, also after injection, due to its material, which is e.g. a gas-impermeable polytetrafluoroethylene (PTFE). The luer-lock connection/septum (vii) suitable for use in the present invention are customary and commercially available.

In a second embodiment of the present invention, the reaction chamber (iii) is executed as a two-compartment reaction chamber, wherein the reaction chamber (iii) is divided into two compartments by a partition wall (viii) (“two-compartment embodiment”). In this embodiment, one compartment comprises the CO-releasing molecule A in solid form, preferably in form of a powder or as a tablet, and the other compartment comprises the CO release triggering compound B, preferably as an aqueous solution. The partition wall (viii) separates the CO releasing molecule A and the CO release triggering compound B during storage and transport of the therapeutic system of the present invention, i.e. before the therapeutic system is used. After fixing the therapeutic system of the present invention to the target site on the skin or the eye of the patient's body, the partition wall (viii) is removed in order to bring the CO releasing molecule A and the CO release triggering compound B into contact in the reaction chamber. The partition wall (viii) can e.g. be removed by pulling it out of the reaction chamber (iii), or alternatively, by breaking by means of applying force to it.

Figure 3:
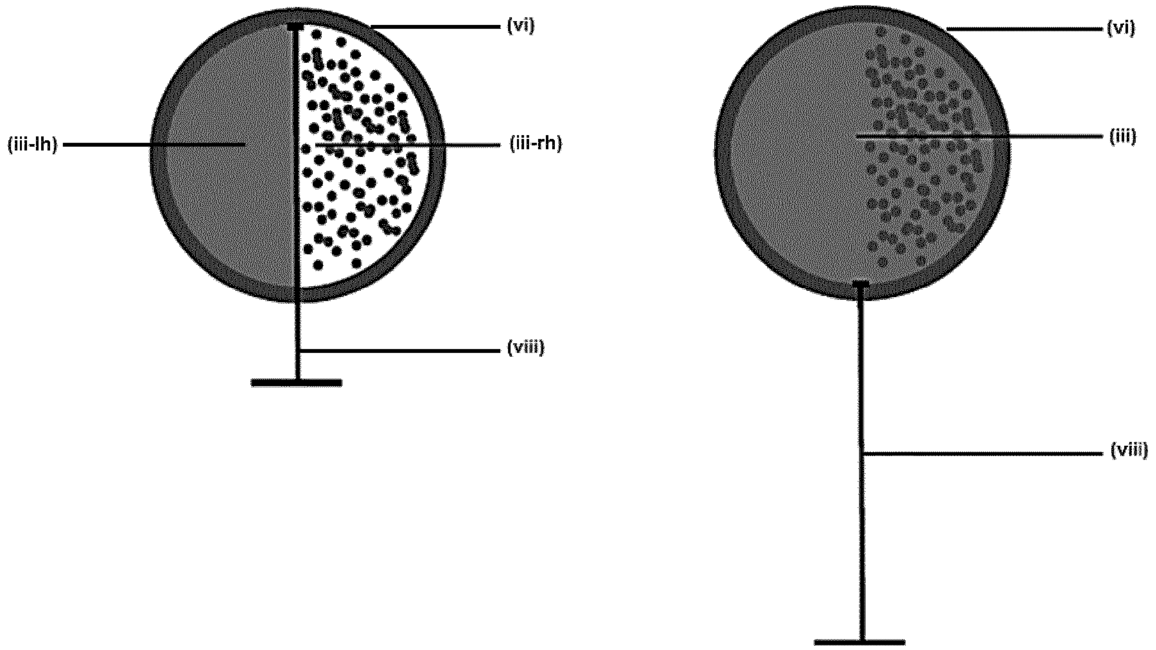
FIG. 3 illustrates the reaction chamber (iii) surrounded by a spacer (vi) in a vertically executed two-compartment embodiment of the therapeutic system of the present invention. The reaction chamber (iii) is divided into two compartments by the partition wall (viii), which on the left hand side of the figure separates the reaction chamber (iii) into a left hand compartment (iii-lh) and a right hand compartment (iii-rh), and which is pulled out on the right hand side of the figure in order to bring the CO releasing molecule A from the CO release triggering compound B into contact in the reaction chamber (iii).
Figure 4:
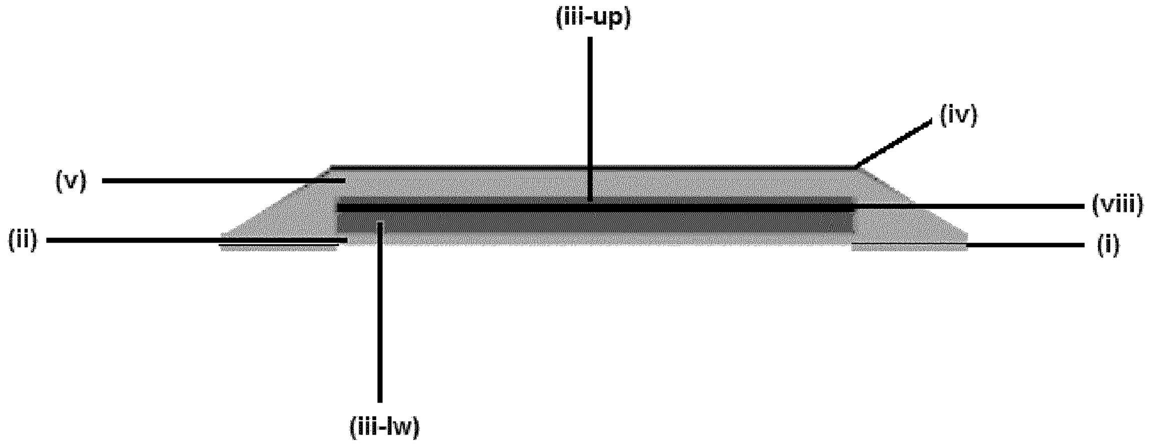
FIG. 4 is a side view on an exemplary horizontally executed two-compartment embodiment of the therapeutic system of the present invention, comprising (i)-(iv), (v), wherein the reaction chamber (iii) is divided into two compartments, one lower compartment (iii-lw) and one upper compartment (iii-up), by a horizontal partition wall (viii), and wherein in accordance with one embodiment of the present invention, the lower membrane (ii) and the upper membrane (v) are connected to form the same component surrounding the reaction chamber (iii).

The separation of the reaction chamber into two compartments by the partition wall (viii) can be executed in a horizontal manner (FIG. 4) or in a vertical manner (FIG. 3), which means that the partition wall (viii) is arranged either horizontally or vertically in the system of the present invention.

In the vertically executed embodiment (FIG. 3), the reaction chamber (iii) is divided into a left-hand compartment (iii-lh) and a right-hand compartment (iii-rh) by the partition wall (viii), wherein one compartment comprises the CO-releasing molecule A in solid form, preferably in form of a powder or as a tablet, and the other compartment comprises the CO-release triggering compound B, preferably as an aqueous solution.

In the horizontally executed embodiment (FIG. 4), the reaction chamber (iii) is divided into a lower compartment (iii-lw) and an upper compartment (iii-up) (as seen from the side of the therapeutic system assuming that the adhesive layer (i) forms the bottom layer and the backing layer (iv) forms the top layer of the system)

In particular the horizontal embodiment allows that the chemical reaction between the CO releasing molecule A and the CO release triggering compound B can be activated by breaking the partition wall (viii) when applying force to it from top of the system (e.g. by means of (manually) squeezing or pressing the system).

The partition wall (viii) is typically made of an inert polymer material, which is preferably a thermoset material (duroplast). Thermoset materials are generally polymers that are irreversibly hardened by curing of liquid or soft viscous pre-polymer material. Curing can e.g. be achieved by applying heat, a catalyst or ultraviolet light, resulting in a crosslinking reaction. Once the pre-polymer material has been cured, it cannot be softened again upon reheating. Particularly preferred as materials for the partition wall (viii) are acrylic resins or epoxy resins as materials for the partition wall (viii). Typically, the partition wall (viii) has a thickness of 0.1-0.4 mm, preferably of 0.15-0.35 mm, more preferably of 0.2-0.3 mm.

The backing layer (iv) of the therapeutic system of the present invention is a gas-impermeable layer on the top side of the therapeutic system, which ensures that no CO is released via the top side of the therapeutic system, thereby protecting the patient from undesired CO loss. The backing layer (iv) is also impermeable to liquids (in particular to water) and to solids. Furthermore, the backing layer serves to protect the therapeutic system from damage during storage and carriage.

The backing layer (iv) can be made of a variety of materials that are gas-impermeable, including, but not limited to, aluminum foil, polyurethane, ethylene vinyl alcohol, ethylene vinyl acetate, polyethylene terephthalate (PET) and polytetrafluoroethylene (PTFE). The preferred material for the backing layer in the present invention is PTFE.

The backing layer (iv) typically a thickness of 0.15-0.45 mm in the system of the present invention, preferably of 0.2-0.4 mm, more preferably of 0.25-0.35 mm.

For the manufacture of the therapeutic system of the present invention, the different layers (adhesive layer (i), membrane (ii), optionally membrane (v), backing layer (iv)) are bonded together using an adhesive, which is preferably a silicon or acrylic adhesive, more preferably a UV-curing or an acetate-crosslinking silicone adhesive. An example for an adhesive that is used in the present invention for the manufacture of the therapeutic system is Loctite® SI 5248. In the course of this process, additional parts such as the spacer (vi), the luer-lock connection/septum (vii) and the partition wall (viii) can be integrated and, if necessary, adhered by an adhesive as described above. The reaction chamber (iii) is also filed with the CO releasing compound A and, optionally, with the CO release triggering compound B during the process of manufacturing of the therapeutic system of the present invention.

CO releasing molecules A and CO release triggering compounds B that are suitable for use in the present invention have been described in WO 2015/188941 A1, WO 2016/110517 A1 and DE 10 2017 006 393 A1.

Preferably, the carbon monoxide releasing molecule (CORM) is a metal carbonyl compound. The metal carbonyl compound comprises e.g. a complex of an element of the group of Rh, Ti, Os, Cr, Mn, Fe, Co, Mo, Ru, W, Re, Ir, B and C. More preferably, the metal carbonyl compound comprises a complex of an element of the group of Rh, Mo, Mn, Fe, Ru, B and C, even more preferably of the group of Rh, Fe, Mn, Mo, B and C. The metal carbonyl compounds may be regarded as complexes, because they comprise CO groups coordinated to a metal center. However, the metal may be bonded to other groups by other than coordination bonds, e.g. by ionic or covalent bonds. Thus, groups other than CO, which form part of the metal carbonyl compound, need not strictly be "ligands" in the sense of being coordinated to a metal center via a lone electron pair, but are referred to herein as "ligands" for ease of reference.

Thus, the ligands to the metal may all be carbonyl ligands. Alternatively, the carbonyl compound may comprise at least one ligand which is not CO. Ligands which are not CO are typically neutral or anionic ligands, such as halide, or derived from Lewis bases and having N, P, O or S or a conjugated carbon group as the coordinating atom(s). Preferred coordinating atoms are N, O and S. Examples include, but are not limited to, sulfoxides such as dimethylsulfoxide, natural and synthetic amino acids and their salts for example, glycine, cysteine, and proline, amines such as $NEt_3$ and $H_2NCH_2CH_2NH_2$, aromatic bases and their analogues, for example, bi-2,2'-pyridyl, indole, pyrimidine and cytidine, pyrroles such as biliverdin and bilirubin, drug molecules such as YC-1 (2-(5'-hydroxymethyl-2'-furyl)-1-benzylindazole), thiols and thiolates such as EtSH and PhSH, chloride, bromide and iodide, carboxylates such as formate, acetate, and oxalate, ethers such as $Et_2O$ and tetrahydrofuran, alcohols such as EtOH, and nitriles such as MeCN. Other possible ligands are conjugated carbon groups, such as dienes, e.g. cyclopentadiene ($C_5H_5$) or substituted cyclopentadiene. The substituent group in substituted cyclopentadiene may be for example an alkanol, an ether or an ester, e.g. $-(CH_2)_nOH$ where n is 1 to 4, particularly $-CH_2OH$, $-(CH_2)_nOR$ where n is 1 to 4 and R is hydrocarbon preferably alkyl of 1 to 4 carbon atoms and $-(CH_2)_nOOCR$ where n is 1 to 4 and R is hydrocarbon preferably alkyl of 1 to 4 carbon atoms. The preferred metal in such a cyclopentadiene or substituted cyclopentadiene carbonyl complex is Fe.

It is also explicitly referred to WO 2008/130261 and US 2007/0219120 A1 for a description of carbon monoxide releasing compounds. There aldehydes according to formula I formula I

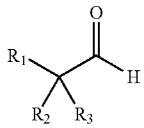

are disclosed which can also be used as therapeutic gas release compound A in the present invention wherein $R_1$, $R_2$ and $R_3$ are each independently selected from alkyl, substituted alkyl, cycloalkyl, substituted cycloalkyl, heterocyclyl, substituted heterocyclyl, alkylheterocyclyl, substituted alkylheterocyclyl, alkenyl, substituted alkenyl, aryl, substituted aryl, heteroaryl, substituted heteroaryl, alkylaryl, substituted alkylaryl, wherein the number of C atoms is 1-12 or 1-6 in each case hydroxy, alkoxy, amino, alkylamino, mercapto, alkylmercapto, aryloxy, substituted aryloxy, heteroaryloxy, substituted heteroaryloxy, alkoxycarbonyl, acyl, acyloxy, acylamino, alkylsulfonyl, alkylsulfinyl, F, Cl, Br, $NO_2$ and cyano; or two or more of $R_1$, $R_2$ and $R_3$ are taken together to form a substituted or unsubstituted carbocyclic or heterocyclic ring structure or an derivative thereof. For any substituent the number of C atoms is 1-12 or 1-6.

A derivative of a compound of formula I being an acetal, hemiacetal, aminocarbinol, aminal, imine, enaminone, imidate, amidine, iminium salt, sodium bissulfite adduct, hemimercaptal, dithioacetal, 1,3-dioxepane, 1,3-dioxane, 1,3-dioxalane, 1,3-dioxetane, α-hydroxy-1,3-dioxepane, α-hydroxy-1,3-dioxane, α-hydroxy-1,3-dioxalane, α-keto-1,3-dioxepane, α-keto-1,3-dioxane, α-keto-1,3-dioxalane, α-keto-1,3-dioxetane, macrocyclic ester/imine, macrocyclic ester/hemiacetal, oxazolidine, tetrahydro-1,3-oxazine, oxazolidinone, tetrahydro-oxazinone, 1,3,4-oxadiazine, thiazolidine, tetrahydro-1,3-thiazine, thiazolidinone, tetrahydro-1, 3-thiazinone, imidazolidine, hexahydro-1,3-pyrimidine, imidazolidinone, tetrahydro-1,3-pyrimidinone, oxime, hydrazone, carbazone, thiocarbazone, semicarbazone, semithiocarbazone, acyloxyalkyl ester derivative, O-acyloxyalkyl derivative, N-acyloxyalkyl derivative, N-Mannich base derivative or N-hydroxymethyl derivative can also be used as carbon monoxide release compound A in the present invention.

The carbon monoxide releasing compound of the present invention can e.g. also be trimethylacetaldehyde, 2,2-dimethyl-4-pentenal, 4-ethyl-4-formyl-hexanenitrile, 3-hydroxy-2,2-dimethylpropanal, 2-formyl-2-methyl-propylmethanoate, 2-ethyl-2-methyl-propionaldehyde, 2,2-dimethyl-3-(p-methylphenyl)propanal or 2-methyl-2-phenyl propionaldehyde.

In one embodiment of the present invention, an oxalate, an oxalate ester or amide is used as carbon monoxide release compound A.

In another embodiment of the present invention, a metal organic framework loaded with a therapeutic gas is used as CO release compound A. Metal-organic frameworks (MOFs) are coordination polymers with an inorganic-organic hybrid frame comprising metal ions and organic ligands coordinated with the metal ions. In one embodiment, the therapeutic gas release compound A is a MOF loaded with at least one CO Lewis base, such as MIL-88B-FE or $NH_2$-MIL-88B-Fe. In another embodiment the therapeutic gas release compound A comprised in the device of the present invention is a MOF loaded with at least one CO Lewis base as described in WO 2009/133278 A1, particularly as described in items 1 to 13 therein to which it is explicitly referred.

Preferred carbon monoxide releasing compounds A for use in the present invention include molybdenum carbonyl compounds, CORM-1, CORM-2, CORM-3, CORM-401, as e.g. disclosed in WO 2015/188941 A1, WO 2016/110517 A1 and DE 10 2017 006 393 A1.

More preferred are molybdenum-based CORMs, such as $Mo(CO)_3(CNC(CH_3)_2COOH)_3$ (also designated as "CORM-ALF794") and $Mo(CO)_3(CNCH_2CO_2H)_3$ (Tricarbonyl[tris(isocyanoaceticacid)]molybdenum(0), also designated herein as "Beck-1"), wherein $Mo(CO)_3(CNCH_2CO_2H)_3$ is particularly preferred. Preferably, $Mo(CO)_3(CNCH_2CO_2H)_3$ is then used as the tri-sodium salt ($Mo(CO)_3(CNCH_2CO_2Na)_3$).

The CO releasing molecule A releases therapeutic gas upon contact with the therapeutic gas release triggering compound B ("trigger compound"). "Contact" means that a reaction between the therapeutic gas release compound A and the trigger compound can take place, which results in CO therapeutic gas release. Upon contact with the trigger compound B, the CO releasing compound A starts to release substantial amounts of gas. The system is then "activated", i.e. release CO through the membrane (ii).

Sulfur-containing compound, nitrogen-containing compounds, oxidizing compounds, metal salts, including oxidizing and non-oxidizing metal salts, acids, bases or water are suitable for use as CO release triggering compounds B in the present invention. If the therapeutic gas release compound A is a metal carbonyl compound, the trigger compound B is preferably selected from the group consisting of sulfur-containing compounds, nitrogen-containing compounds, oxidizing compounds, metal salts, including oxidizing metal salts, and water.

The sulfur-containing compound can then e.g. be selected from an alkali metal or alkaline-earth metal salt, preferably a sodium salt of sulfite, dithionite, or metabisulfite, or a compound bearing at least one thiol moiety, such as cysteine or glutathione.

Examples of oxidizing compounds to be used as CO release trigger compounds B in the present invention include peroxides, perborates, percarbonates, and nitrates of which calciumperoxide, di benzoyl peroxide, hydrogen peroxide urea, sodium perborate, and sodium percarbonate are preferred.

Metal salts including oxidizing metal salts that can be used as trigger compounds include and silver(I)nitrate, iron (III)chloride, potassium permanganate, cer(IV)sulfate, potassium dichromate, gold(III)chloride and silver nitrate, wherein iron(III)chloride, potassium permanganate and cer (IV)sulfate and, in particular, iron(III)chloride and cer(IV) sulfate, are preferred. The metal salts including oxidizing metal salts are preferably used in aqueous solution.

In preferred embodiments of the present invention, molybdenum carbonyl compounds are used as the CO releasing compound A and oxidizing compounds and metal salts, including oxidizing metal salts, are used as the CO release triggering compound B. In a further preferred alternative preferred embodiment, CORM-2 ($Ru_2(CO)_6Cl_4$) is used as the therapeutic gas releasing compound A and sodium sulfite ($Na_2SO_3$) is used as the therapeutic gas release triggering compound B.

Particularly preferred embodiments include combinations of a molybdenum carbonyl compounds, preferably Mo(CO)

$_3(CNCH_2COOH)_3$ (Beck-1), with iron(III)chloride ($FeCl_3$), cer(IV)sulfate ($Ce(SO_4)_2$) or $H_2O_2$, wherein $FeCl_3$ and $Ce(SO_4)_2$ are used as aqueous solutions at concentrations from 2-3 mol/L, and $H_2O_2$ is used as aqueous solution at a concentration of 30 wt.-% Molybdenum carbonyl compounds have the advantage of producing CO at a high capacity (≥95%) and with a high purity (>95%). For achieving a particularly high CO production with a particularly high purity, it is particularly preferred to use Beck-1 ($Mo(CO)_3(CNCH_2COOH)_3$) in combination with $FeCl_3$.

The therapeutic gas release system of the present invention releases a therapeutic gas in a therapeutically effective amount when administered to a patient. In a preferred embodiment, the therapeutic system of the present invention releases between 0.1 and 100 μmol of carbon monoxide to a patient.

The amount of therapeutic gas to be released from the therapeutic gas release system of the present invention can be tailored, e.g. by the chemical nature and amount of therapeutic gas release compound A and by the chemical nature and amount of the trigger compound B.

Typical weight amounts for the therapeutic gas release compound A in the system of the present invention range from 1-200 mg, preferably 5-100 mg, more preferably 10-50 mg. Typical molar amounts for the therapeutic gas release compound A range from 5-100 μmol, preferably 10-60 μmol more preferably 20-40 μmol.

The gas release triggering compound B can be used in amounts up to the 100-fold molar excess relative to the therapeutic gas release compound A, with preferred amounts ranging from 5 to 75-fold molar excess, more preferably 10 to 50-fold molar excess relative to the therapeutic gas release compound A.

Preferably, the therapeutic gas release triggering compound B is used in aqueous solution or suspension because the chemical reaction between compound A and compound B upon proceeds better in solution or in a suspension. Typical concentrations for the therapeutic gas release triggering compound B range from 0.5-10 mol/L, preferably 1-5 mol/L, more preferably 2-3 mol/L.

It is preferred to use 1 ml of the aqueous solution of gas release triggering compound B per 10 mg CORM contained in the therapeutic system, and the concentration of the aqueous solution is chosen accordingly. The release rate of the CO therapeutic gas from the system of the present invention can be tailored by means of the thickness of the membrane (ii). The release rate of the CO therapeutic gas can furthermore be tailored by the form in which the CO-releasing molecule A is used in the therapeutic system of the present invention. If the CO-releasing molecule A is for example provided in form of a tablet, it can additionally be coated with a modified release coating that decreases the release rate of the CO therapeutic gas from the therapeutic system of the present invention. On the other hand, if the CO-releasing molecule A is e.g. used in form of a powder, the release rate of CO therapeutic gas from the system of the present invention is increased.

The absolute amount of CO released from the therapeutic system of the present invention can be tailored by the amount of CO releasing compound contained in the system as well as the amount of CO-release triggering compound B brought into contact with the CO-releasing molecule A in the reaction chamber (iii).

The contact surface and geometry of the therapeutic system is scalable and variable and can be adjusted to the size of the target site, such as the size of a wound, as well as to the amount of CO releasing compound A required. The therapeutic system of the present invention can e.g. be provided in a rounded shape (i.e. circular or oval) or in an angular shape (i.e. square or rectangular). If provided in a rectangular shape, the edge lengths of the therapeutic system are typically 30-70 mm×30-70 mm, preferably 35-65 mm×35-65 mm, more preferably 40-60 mm×40-60 mm. If provided in a circular shape, the diameter of the therapeutic system is typically 30-70 mm, preferably 35-65 mm, more preferably 40-60 mm.

The thickness of the therapeutic system of the present invention typically ranges from 3-15 mm. In one-compartment embodiment, wherein the therapeutic system additionally comprises a luer-lock connection (vii) or a septum (vii) in order to allow addition of the gas release triggering compound B into the reaction chamber by means of an injection device, the system of the present invention is provided with greater thicknesses, ranging typically from 7-15 mm, preferably 9-13 mm, in order to allow the luer-lock connection (vii) and the septum (vii), respectively to be integrated into the system. In the two-compartment embodiment, which does not require an integrated luer-lock connection or septum (vii), the therapeutic system of the present invention typically has a thickness of 3-7 mm, preferably 4-6 mm. Particularly the two-compartment embodiment with its reduced thickness can be comfortably carried by the patient, without affecting him or her too much.

The transdermal therapeutic system can also be provided with tapered side walls, wherein the size of the layers decreases from the bottom to the top of the system. This increases the stability of the therapeutic system when fixed to the target site of the patient's body.

The application time of the therapeutic system according to the present invention is typically 1-5 days, preferably 1.5-4 days, more preferably 2-3 days.

The therapeutic system of the present invention enables the local (topic) application of CO as a therapeutic gas directly into wound tissue to accelerate wound healing processes.

The therapeutic system of the present invention can furthermore be used for the treatment of inflammatory diseases of the skin, such as dermatitis and eczema. The therapeutic system of the present invention overcomes the disadvantages of ointment and creams which are currently used in the therapy of these diseases. These often contain glucocorticoids that bear a high risk for side effects, in particular in the long term application. The CO releasing therapeutic system of the present invention uses the anti-inflammatory properties of CO for the treatment of inflammatory skin diseases at a much lower risk for the patient in terms of the occurrence of side effects, which makes the therapeutic system of the present invention particularly useful for long term application of such diseases.

Due to the ability of CO to penetrate intact layers of the skin, the present invention furthermore enables the transdermal and transcutaneous application of CO into subcutaneous skin tissue, as well as to tendons and joints. This enables use of the system of the present invention in the treatment of inflammatory diseases associated with subcutaneous skin tissue, as well as to tendons and joints, such as e.g. gout and tendinitis, e.g. tendinitis of the Achilles tendon. The joints and tendons affected by these disorders are well-attainable with the therapeutic system of the present invention as the skin and subcutaneous skin tissue are relatively thin so that a very good penetration of the CO therapeutic gas to the affected sites can be achieved through the skin and subcutaneous tissue layers.

The advantage of using the therapeutic system of the present invention for the treatment of diseases associated with subcutaneous skin tissue, tendons and joints is a significantly improved bioavailability of the active substance and a direct mechanism of action compared to conventional NSAIDs (nonsteroidal anti-inflammatory drugs) such as ibuprofen and diclofenac, which positively influences the disease and the healing process, respectively.

The therapeutic system of the present invention also has the advantage that compared to conventional NSAIDs, ointments and creams typically used for the treatment of inflammatory diseases of the skin and subcutaneous sites, such as subcutaneous skin tissue, tendons and joints, no excipients, additives or degradation products come into direct contact with the skin or subcutaneous tissue, and accordingly, side effects are reduced or avoided.

For the first embodiment of the present invention, the one-compartment therapeutic system, a kit is provided comprising said one-compartment therapeutic system of the present invention and an injection device, which is preferably a customary syringe. The injection device comprises the CO release triggering compound B as an aqueous solution or suspension, preferably as an aqueous solution, which is injected into the reaction chamber (iii) via the luer-lock connection/septum (vii) of the therapeutic system as described above. Typically, the injection device, preferably the syringe, holds a volume of 1-5 ml of the aqueous solution or suspension.

The following examples are intended to illustrate the present invention without limiting its scope.

EXAMPLES

Example 1: CO Release Through Pig Ear Skin

Figure 5:
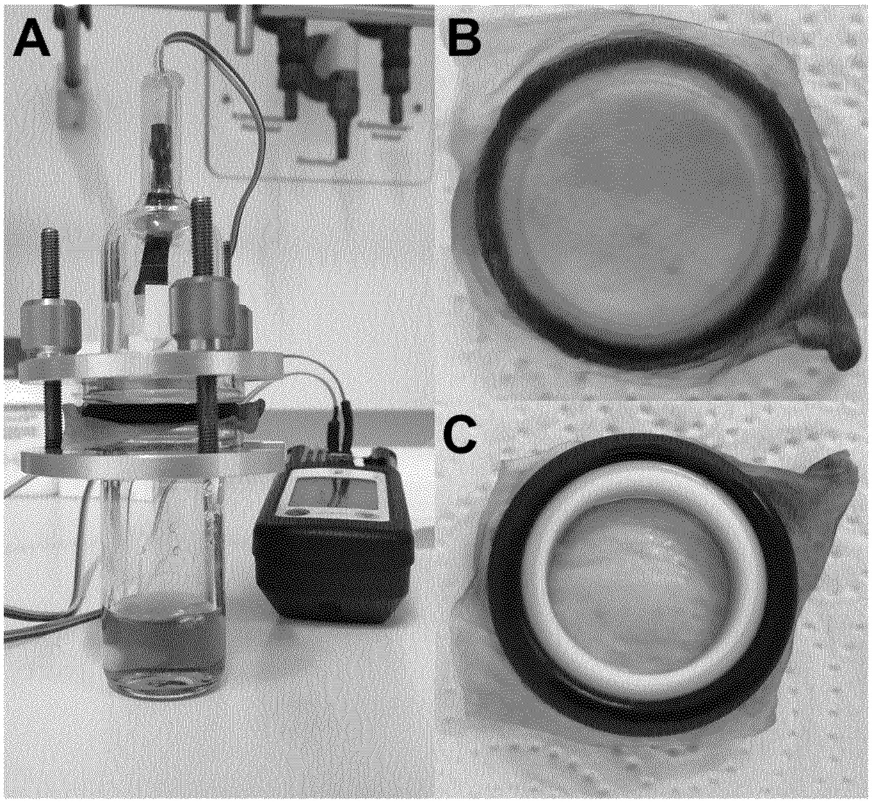
FIG. 5 shows an experimental setup for determining CO release through pig ear skin: (A) pig ear skin clamped between the top and bottom compartment of the test cell. (B) Upper surface of the pig ear skin after 1000 minutes of CO release through the skin. (C) Lower surface of the pig ear skin after 1000 minutes of CO release through the skin.

Pig ear skin was purchased from a butcher and prepared immediately after delivery. Skin was carefully removed from the remaining fat and cartilage. Subsequent to the preparation, the skin was clamped between the top and bottom compartment of the test cell. Sealing was ensured by screw clamps and a sealing ring (FIG. 5A).

For the experiment 15 mg of tri-sodium Beck-1 ($(Mo(CO)_3(CNCH_2CO_2Na)_3)$) were placed in the bottom compartment of the test cell and dissolved in 4 mL $H_2O$. CO release was activated by adding 1 mL of iron(III)chloride solution (350 mg/mL) to the tri-sodium Beck-1. CO release through the pig skin was measured over a time period of 1000 minutes.

After the experiment the skin was dried out at the parts hanging over the sealing ring. The inside and especially the lower surface of the pig ear skin was still moist and intact (FIGS. 5B and 5C).

Figure 6:
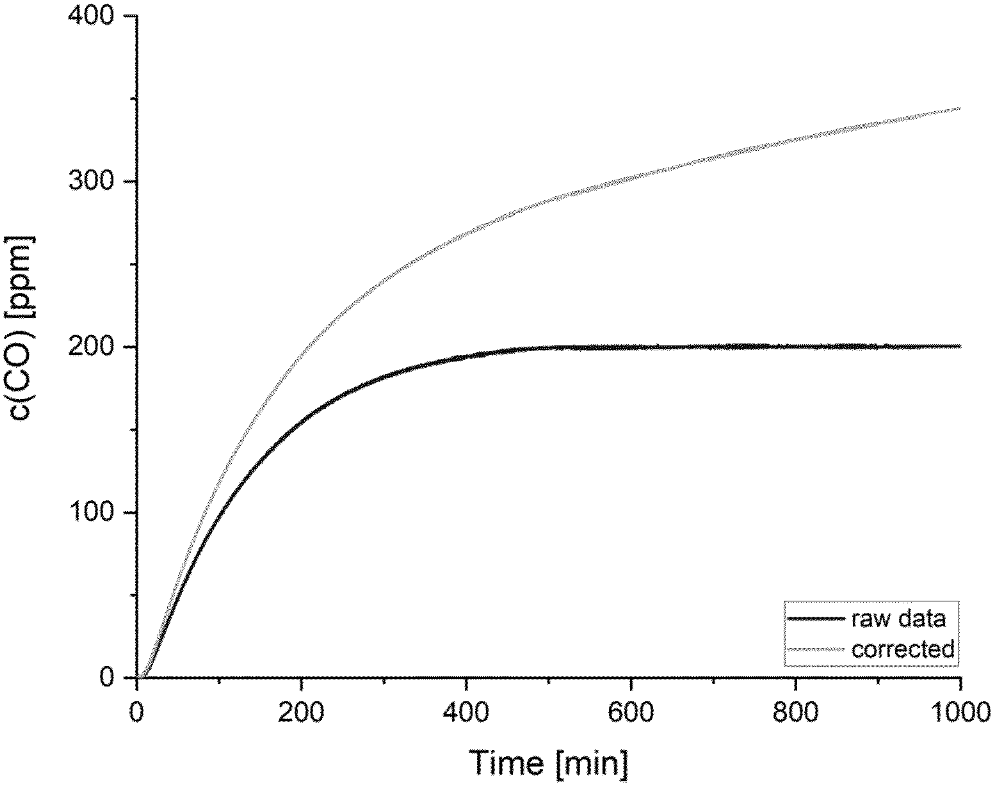
FIG. 6 shows the averaged raw data (n=2) for CO release through pig ear skin over 1000 minutes and the corrected data.

The data shown in FIG. 6 illustrates that CO release trough the pig skin is a slow process and reaches plateau in the raw data at around 500 minutes and stays at that plateau of 200 ppm CO for another 500 minutes until the end of the experiment. A plateau in the raw data means that the sensor consumption of CO is at the same rate as the release through the skin. To correct for the sensor consumption, CO release data of tri-sodium Beck-1 without any limiting membranes were used to calculate the consumption rate of the sensor.

The corrected data in FIG. 6 show that over a period of 1000 minutes a release of CO through the pig skin can be detected, reaching a maximum of 340 ppm at that point. The data suggest that even higher final CO concentrations can be achieved as long as no decrease in CO concentration is observed in the raw data.

All in all, the data show that releasing CO gas through ear skin of pigs is possible. Since the release through dead skin of pigs serves as a model for penetration studies of transdermal patches, it can safely be assumed that release of CO gas through live human skin will also be possible.

Example 2: CO Release into Pig's Eye

In order to assess CO release into the eye, the therapeutic system of the present invention is used on pig eyes (post mortem). For this purpose, fresh pig eyes, stored in Krebs Henseleiten solution immediately after removal, are used. Excess muscle tissue is removed from the pig's eye and a solution of carbon monoxide detecting reagent is given intravitreally into the eye. The therapeutic system of the present invention is activated and placed on the cornea of the pig's eye. In order to determine the diffusion of the CO through the various areas of the eye, the retina is removed from the pig's eye after the diffusion experiment, and analyzed microscopically.

The invention claimed is:

1. A therapeutic system for the topical, transdermal and transcutaneous application of carbon monoxide (CO), said system comprising:

(i) an adhesive layer, (ii) a gas-permeable and liquid- and solid-impermeable membrane, (iii) a reaction chamber comprising a CO releasing molecule A, and (iv) a gas-impermeable backing layer, wherein the therapeutic system is configured such that the CO releasing molecule A can be brought into contact with a CO release triggering compound B in the reaction chamber (iii), wherein the CO releasing molecule A is a molybdenum carbonyl compound, and wherein the reaction chamber (iii) is surrounded by a spacer made of silicone.

2. The therapeutic system according to claim 1, wherein the membrane (ii) is a lower membrane and the system additionally comprises a liquid- and solid-impermeable upper membrane (v) disposed between the reaction chamber (iii) and the backing layer (iv).

3. The therapeutic system according to claim 1, wherein the membrane is fabricated from an expanded polytetrafluoroethylene or silicone.

4. The therapeutic system according to claim 1, wherein the reaction chamber (iii) is a one-compartment reaction chamber and the therapeutic system further comprises a luer-lock connection (vii) or a septum (vii) that allows for addition of a CO release triggering compound B into the reaction chamber (iii).

5. The therapeutic system according to claim 1, wherein the reaction chamber (iii) is a two-compartment reaction chamber divided by a removable partition wall (viii), further wherein a first of said two compartments comprises the CO releasing molecule A, and a second of said two compartments comprises the CO-release triggering compound B.

6. The therapeutic system according to claim 1, wherein the adhesive layer is protected by a release liner during storage of the therapeutic system.

7. The therapeutic system according to claim 1, wherein the CO release triggering compound B is selected from the group consisting of a sulfur containing compound, a nitrogen containing compound, an oxidizing compound, an oxidizing metal salt, a non-oxidizing metal salt, and water.

8. The therapeutic system according to claim 1, wherein the CO release triggering compound B is selected from the group consisting of $FeCl_3$, $Ce(SO_4)_2$ and $H_2O_2$, preferably $FeCl_3$.

9. The therapeutic system according to claim 1, wherein the CO releasing molecule A is used in form of a powder or tablet and/or the CO release triggering compound B is used in form of an aqueous solution or suspension.

10. A method for treating a wound, said method comprising the step of applying the therapeutic system according to claim 1 to the wound of a patient in need of such treatment.

11. A method for treating an inflammatory disease of the skin, said method comprising the step of applying the therapeutic system according to claim 1 to an afflicted area of a patient's skin in need of such treatment.

12. A method for treating an inflammatory disease of the subcutaneous skin tissue, tendons and/or joints, said method comprising the step of applying the therapeutic system according to claim 1 to an afflicted tissue of a patient in need of such treatment.

13. A method for treating an inflammatory disease of the eye, said method comprising the step of applying the therapeutic system according to claim 1 to one or both eyes of a patient in need of such treatment.

14. A kit comprising the therapeutic system according to claim 1 in combination with an injection device, wherein said injection device carries an aqueous solution of the CO release triggering compound B.

15. The kit of claim 14, wherein said injection device is a syringe.

16. The therapeutic system according to claim 1, wherein the membrane is fabricated from silicone.

17. The therapeutic system according to claim 8, wherein the CO releasing molecule A is $Mo(CO)_3(CNCH_2CO_2H)_3$ and the CO release triggering compound B is $FeCl_3$.

18. The method according to claim 11, wherein said inflammatory disease of the skin is dermatitis or eczema.

19. The method according to claim 12, wherein said inflammatory disease of the subcutaneous skin tissue, tendons and/or joints is gout and tendonitis.

20. The system according to claim 1, wherein said silicone spacer reinforces said reaction chamber while affording sufficient overall flexibility to said therapeutic system to enable application to an afflicted tissue site.

* * * * *